United States Patent
Ravenscroft et al.

(10) Patent No.: US 7,056,286 B2
(45) Date of Patent: Jun. 6, 2006

(54) MEDICAL DEVICE ANCHOR AND DELIVERY SYSTEM

(76) Inventors: Adrian Ravenscroft, Phase-One Medical, LLP, 124 Main St., Suite F, Carver, MA (US) 02330; Stephen J. Kleshinski, Phase-One Medical, LLP, 124 Main St., Suite F, Carver, MA (US) 02330

( * ) Notice: Subject to any disclaimer, the term of this patent is extended or adjusted under 35 U.S.C. 154(b) by 184 days.

(21) Appl. No.: 10/705,226

(22) Filed: Nov. 12, 2003

(65) Prior Publication Data

US 2005/0101982 A1 May 12, 2005

(51) Int. Cl.
*A61M 29/00* (2006.01)
(52) U.S. Cl. ...................................... 600/200
(58) Field of Classification Search ................ 606/200, 606/151, 153, 157, 219, 213; 623/1.15
See application file for complete search history.

(56) References Cited

U.S. PATENT DOCUMENTS

| | | |
|---|---|---|
| 4,425,908 A | 1/1984 | Simon |
| 4,592,356 A | 6/1986 | Gutierrez |
| 4,616,656 A | 10/1986 | Nicholson et al. |
| 4,774,949 A | 10/1988 | Fogarty |
| 4,790,329 A | 12/1988 | Simon |
| 4,817,600 A | 4/1989 | Herms et al. |
| 4,986,279 A | 1/1991 | O'Neill |
| 5,018,530 A | 5/1991 | Rank et al. |
| 5,108,418 A | 4/1992 | Lefebvre |
| 5,127,916 A | 7/1992 | Spencer et al. |
| 5,133,733 A | 7/1992 | Rasmussen et al. |
| 5,158,565 A | 10/1992 | Marcadis et al. |
| 5,242,462 A | 9/1993 | El-Nounou et al. |
| 5,370,657 A | 12/1994 | Irie |
| 5,601,595 A | 2/1997 | Smith |
| 5,800,457 A | 9/1998 | Gelbfish |
| 5,853,420 A | 12/1998 | Chevillon |
| 6,007,558 A | 12/1999 | Ravenscroft et al. |
| 6,231,589 B1 * | 5/2001 | Wessman et al. ............ 606/200 |
| 6,258,026 B1 | 7/2001 | Ravenscroft et al. |
| 6,447,530 B1 | 9/2002 | Ostrovsky et al. |
| 2004/0249408 A1 * | 12/2004 | Murphy et al. ............. 606/198 |

* cited by examiner

*Primary Examiner*—(Jackie) Tan-Uyen T. Ho
(74) *Attorney, Agent, or Firm*—Nixon Peabody LLP

(57) ABSTRACT

A method and apparatus for anchoring a medical implant device after the device has been brought to rest at a desired position within a blood vessel or other body passageway. An anchor delivery system is provided which houses one or more uniquely configured expandable anchors which are connected to the medical implant device. The anchors remain housed in a non expanded configuration until after the medical implant device has come to rest in a desired position within the body, and then the anchors are positively propelled through a body wall from a first side to a second side where each anchor expands outwardly on opposite sides of an anchor shaft. To positively propel the anchors, a drive shaft for the anchor shafts extends back to a triggering unit which, when activated, causes the drive shaft to drive the anchor shafts in a direction which results in propulsion of the anchors through the body wall.

36 Claims, 5 Drawing Sheets

FIG. 10
FIG. 9
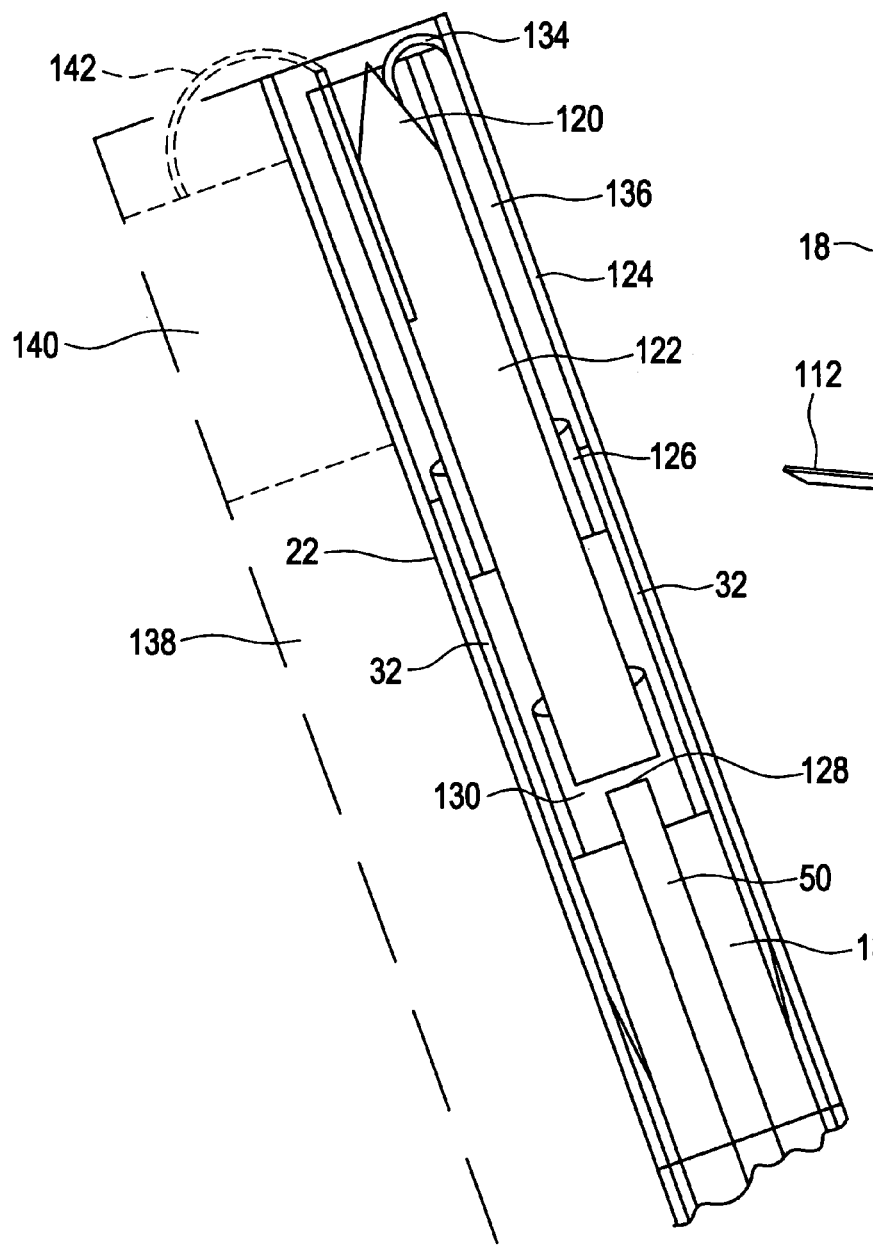
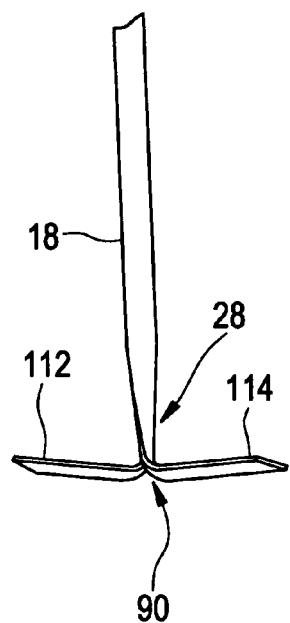

MEDICAL DEVICE ANCHOR AND DELIVERY SYSTEM

BACKGROUND OF THE INVENTION

Recent advances in medical technology have resulted in the development of a variety of medical devices for permanent or temporary implantation in the human body. Effective positioning of such devices can prove to be a very difficult task, and maintaining an implanted device in a desired position for an extended period of time is often more difficult. This is particularly true if the implanted device is to remain only temporarily and is designed to facilitate subsequent removal.

A number of medical implant devices are designed to collapse for insertion within a catheter or other delivery unit and to expand to a predetermined shape when ejected after delivery. Many of these self expanding devices rely primarily upon the contact between the device and the wall of a body vessel or passageway to maintain the device in position after the delivery unit is removed. Unfortunately, changes in the configuration of the body vessel or passageway or variations in the flow of blood or other fluids there through can cause the medical implant to migrate and change position.

It is extremely important that a medical implant device be properly positioned and oriented, and that this position and orientation be maintained. Otherwise, effective performance of such therapeutic devices will not be achieved. It is often very difficult to move such a device into position with the desired orientation, and once this is achieved, it is critical that no further motion occur.

In an attempt to prevent migration of a medical implant device, rigid hooks are often formed on the device to engage the wall of a body vessel or passageway as the implant device expands into contact with the wall. After a few weeks, the endothelium layer grows over rigid hooks which will not easily bend under the influence of withdrawal pressure, and the medical implant device will be locked in place by the embedded hooks. This may be acceptable for a permanent implant, but rigid hooks are not a viable option if the medical implant device is to be removed after several weeks or months.

To facilitate removal of a previously implanted medical device by withdrawal of the anchoring hooks from an enveloping endothelium layer without risking substantial damage to the wall of a body vessel or passageway, the hooks have been formed to straighten when subjected to a withdrawal force greater than a maximum migration force. U.S. Pat. Nos. 6,007,558 and 6,258,026 to Ravenscroft, et al show hooks which are formed to bend and straighten in response to a withdrawal force, while U.S. Pat. No. 4,425,908 to Simon, U.S. Pat. No. 4,817,600 to Herms, et al, U.S. Pat. No. 5,108,418 to Lefebvre, U.S. Pat. No. 5,133,733 to Rasmussen, et al, U.S. Pat. No. 5,242,462 to El-Nounou, et al, U.S. Pat. No. 5,370,657 to Irie, U.S. Pat. No. 5,601,595 to Smith, U.S. Pat. No. 5,800,457 to Gelbfish, and U.S. Pat. No. 5,5853,420 to Chevillon, et al all disclose expandable medical implant devices; many with anchoring hooks.

Anchoring hooks, although effective in many instances, are subject to a number of disadvantages which can make it difficult to properly position and maintain the position of a medical implant device. In prior devices, the anchoring hooks are engaged due to the expansion of the device into contact with the wall of a body vessel or passageway, and if the device moves from a desired position during expansion and contact with the wall occurs, the device cannot be easily repositioned. The anchoring function of the hooks is not separable from the expansion of the device.

In cases where the operation of the hooks is tied to the expansion of a medical implant device, there can be instances where one or more of the hooks fails to properly pierce the wall of a body vessel or passageway causing the device to become off center. Sometimes movement of the device longitudinally will engage the errant hooks, but this movement can also alter the position of the device.

Finally, the configuration of a hook which curves in a single direction from a shaft to a pointed end can prove to be a disadvantage. When hooks are used to anchor a medical implant device within a blood vessel, it is important that the hook be oriented to curve in the direction of normal blood flow through the vessel as it engages the vessel wall. Thus when engaged, the hook will extend from the shaft toward the point substantially in the direction of the longitudinal axis of the blood vessel, and will effectively resist migration of the medical implant device in response to pressure thereon from blood flow in the normal direction through the blood vessel. However, there are conditions which can result in a backflow of blood in a blood vessel, and pressure on the device and the anchoring hooks resulting from such backflow can cause the hooks to back out and disengage from the vessel, thus changing the orientation of the device within the blood vessel and causing deleterious changes in the performance of the implant.

SUMMARY OF THE INVENTION

It is a primary object of the present invention to provide a novel and improved method for positioning and anchoring a medical implant device which includes positively propelling one or more anchors through a body wall subsequent to a medical implant device connected to the anchor reaching a desired position and coming to rest.

Another object of the present invention is to provide a novel and improved medical device anchor and delivery system wherein one or more anchors are positively propelled through a body wall. Once an anchor has passed through the wall, it expands outwardly from at least two opposed sides of an anchor shaft.

An additional object of the present invention is to provide a novel and improved medical device anchor designed to penetrate a body wall from a first side to a second side and to expand outwardly from at least two opposed sides of an anchor shaft after penetration.

Another object of the present invention is to provide a novel and improved medical device anchor designed to penetrate the wall of a body vessel from a first side to a second side and to expand outwardly from at least two opposed sides of an anchor shaft in a unique manner after penetration. The expanded anchor is designed to be loaded in compression against the second wall of the vessel in response to forces normal to the longitudinal axis of the vessel which are applied to a medical device attached to the anchor.

A further object of the present invention is to provide a novel and improved medical device anchor and delivery system wherein one or more anchors are positively propelled through a body wall subsequent to a medical implant device connected to the anchors reaching a desired position and coming to rest. The anchor delivery system facilitates removal and reinsertion of the anchors without requiring that the medical implant device connected thereto be compressed and/or removed.

Yet another object of the present invention is to provide a novel and improved anchor and anchor delivery system for a medical implant device to anchor the device in position within a blood vessel or other body passageway. Once the medical implant device has been positioned and expanded into contact with the wall of the blood vessel or body passageway, the anchor delivery system then positively propels one or more anchors through the vessel or passageway wall where the anchors expand outwardly on opposite sides of an anchor shaft. The anchor delivery system permits the anchors to be withdrawn and then reinserted through the wall without the necessity to collapse the medical implant device.

A further object of the present invention is to provide a novel and improved anchor and anchor delivery system for a medical implant device to anchor the device in position within a blood vessel or other body passageway while facilitating the subsequent withdrawal of the device. The anchor delivery system positively propels one or more anchors through the wall of a blood vessel or body passageway once the medical implant device has expanded into contact with the wall, and the anchors then expand outwardly from opposite sides of an anchor shaft. The anchors are formed to contract back toward the longitudinal axis of the anchor shaft in response to a predetermined force to permit withdrawal through the wall.

A still further object of the present invention is to provide a novel and improved anchor and anchor delivery system for a blood clot filter where the delivery system includes elongate, tubular filter legs which house the anchors. Once the filter legs are ejected from a catheter or delivery tube and expand into contact with the blood vessel wall, the anchor delivery system positively propels the anchors outwardly from the filter legs and through the blood vessel wall from a first side to a second side where the anchors expand outwardly on opposite sides of an anchor shaft against the second side of the wall. Each anchor is formed to contract back toward the longitudinal axis of its anchor shaft in response to a predetermined force to permit withdrawal through the wall, and this permits the anchors to be withdrawn back into the filter legs and then again propelled through the blood vessel wall without collapsing the filter legs.

These and other objects of the present invention are achieved by providing an anchor delivery system which houses one or more uniquely configured anchors which are connected to a medical implant device. The anchors remain housed until after the medical implant device has come to rest in a desired position within a body, and then the anchors are positively propelled through a body wall from a first side to a second side where each anchor expands from a single shaft configuration outwardly on opposite sides of an anchor shaft. To propel the anchors, a drive shaft extends from an anchor support sleeve back to a triggering unit which, when activated, causes the drive shaft to move the anchor support sleeve in a direction to propel the anchors through the body wall. The triggering unit may be spring powered or solenoid powered.

BRIEF DESCRIPTION OF THE DRAWINGS

FIG. 9 is a perspective view of a third embodiment of a deployed anchor of the present invention; and FIG. 10 is a sectional view of a single anchor and anchor delivery system of the present invention.

DETAILED DESCRIPTION

Figure 1:
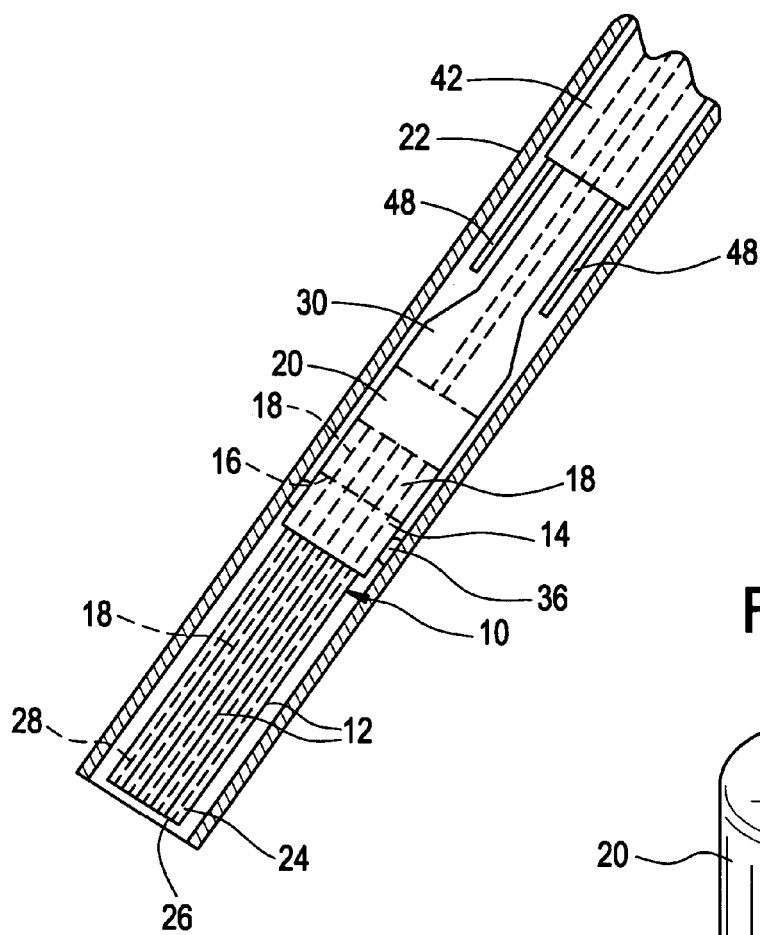
FIG. 1 is a sectional view showing a blood clot filter with anchors formed in accordance with the present invention mounted within a catheter.
Figure 2:
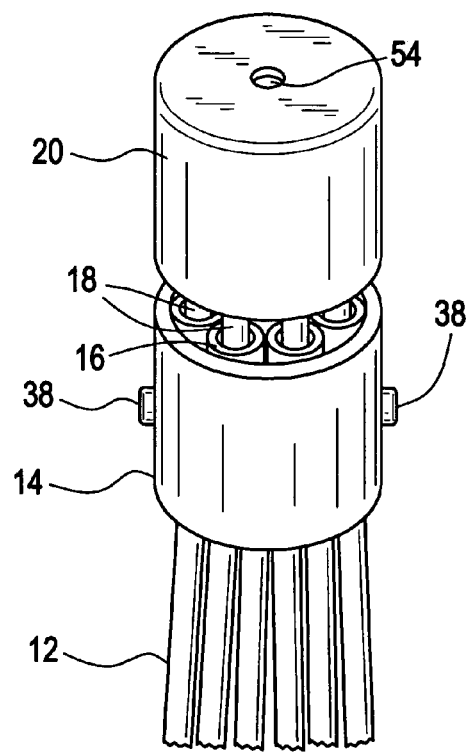
FIG. 2 is a perspective view showing the anchor support hub and leg retention sleeve of FIG. 1.

Referring to FIGS. 1–2, a blood clot filter which includes anchors in accordance with the present invention is illustrated generally at 10. This filter, shown for illustration as a vena cava filter, is formed with a plurality of elongate legs 12 which are secured to, and extend outwardly from a leg retention sleeve 14. The elongate legs are formed by small, open ended tubes each having a first open end 16 which opens at the leg retention sleeve. A plurality of long shafts 18 are attached at a distal end to an anchor support hub 20 which is spaced from the leg retention sleeve when the vena cava filter is collapsed within a catheter or delivery tube 22. Each shaft 18 extends from the anchor support hub 20 into the first open end 16 of a tubular leg 12 and through the leg to a distal end 24 at a point adjacent to a second open end 26 of the tubular leg. An anchor 28 is formed at the distal end of each shaft 18 in a manner to be described.

Figure 6:
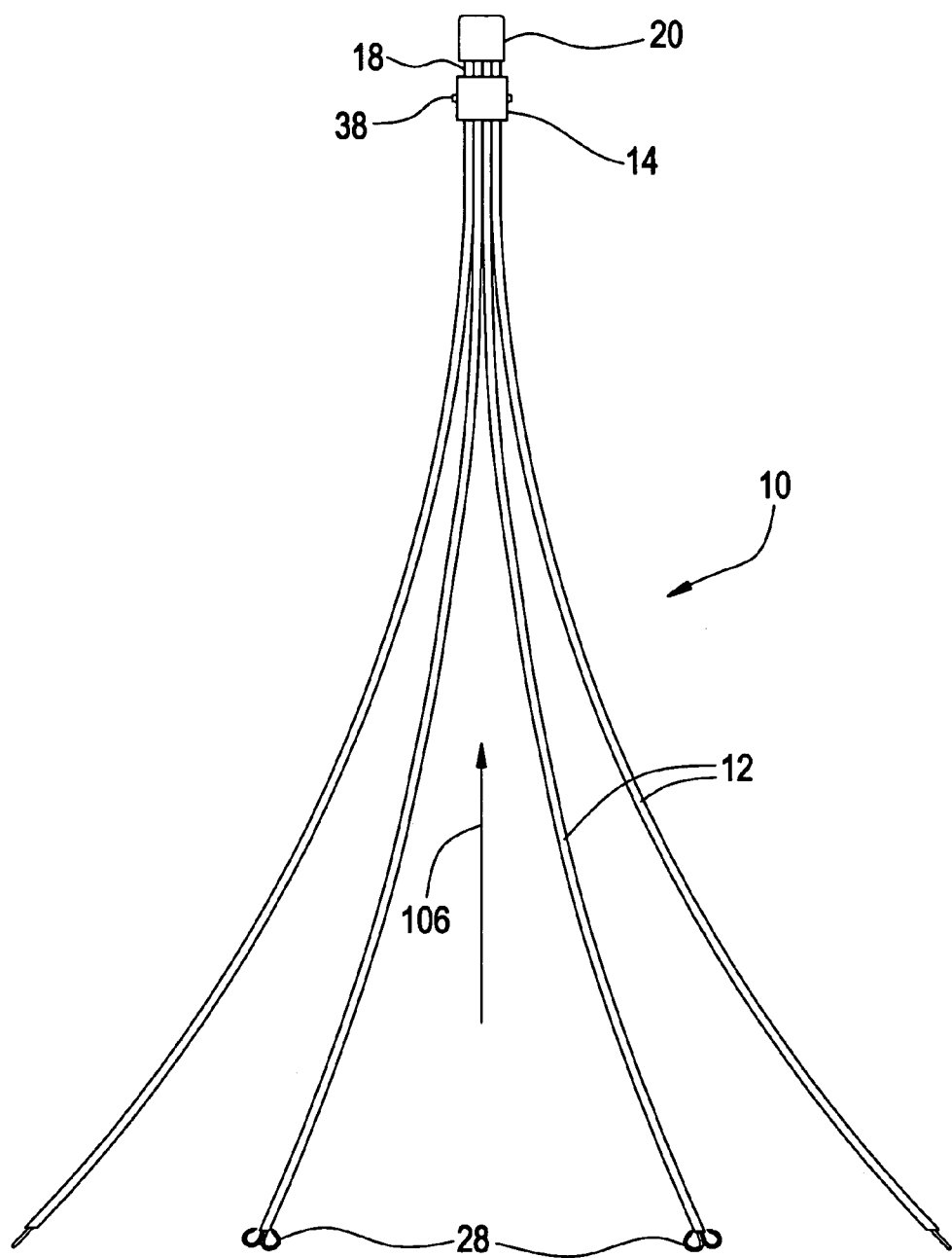
FIG. 6 is a perspective view of the deployed blood clot filter of FIG. 1.

The elongate legs 12 and the long shafts 18 are formed of a material which will permit them to be compressed toward the longitudinal axis of the filter 10 for delivery by a catheter 22. Once the filter is ejected from the catheter, the legs 12 and the shafts 18 are designed to expand outwardly from the filter longitudinal axis as shown in FIG. 6 to bring the legs into contact with the wall of a blood vessel. Although spring metal and suitable plastics can be used to form the legs 12 and/or the shafts 18, it is preferable to form the shafts 18 and in most cases the legs 12 of a suitable shape memory material. If a temperature responsive shape memory material such as nitinol is used, transition between the martensitic and austenitic states of the material can be achieved by temperature transitions relative to a transition temperature. In the martensitic state, the material softens, thereby permitting a filter formed thereof to be compressed and loaded into a catheter. If the transition temperature of the material is set at, or near to normal body temperature, then the filter legs will pass to the austenitic state when the filter is ejected from the catheter and expand to regain a memorized shape.

Figure 3:
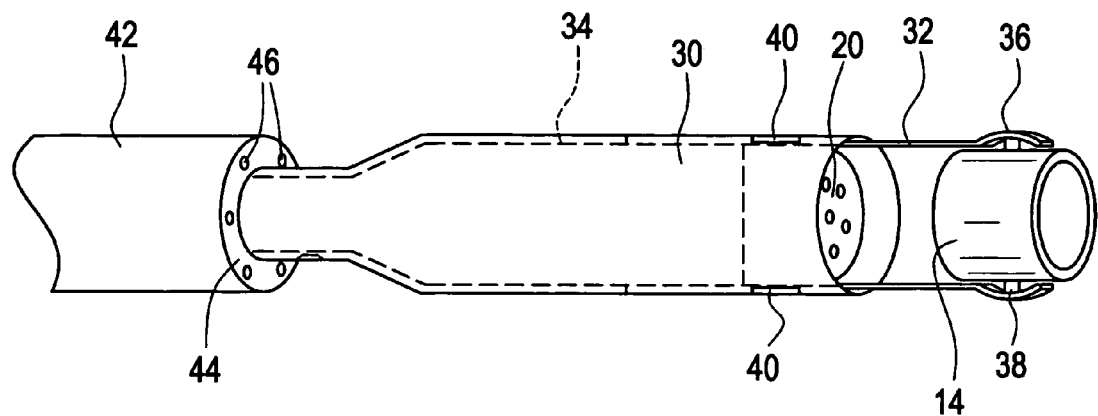
FIG. 3 is a perspective view showing the locking sleeve for the leg retention sleeve of FIG. 2.

For delivery through the catheter 22, the leg retention sleeve 14 is locked to the anchor support hub 20 by a locking sleeve 30 which surrounds both the anchor support hub and the leg retention sleeve when in the locking position as shown in FIG. 1. In the unlocked position, the locking sleeve is moved longitudinally back away from the leg retention sleeve as shown in FIG. 3. Two spring arms 32 are connected at one end to a housing 34 behind the anchor support hub and extend outwardly over opposite sides of the leg retention sleeve. The free end of each of the spring arms is curved to form an arcuate latch member 36 which overlies and, in the locking position of FIG. 1, engages a locking projection 38 formed on the leg retention sleeve. When the locking sleeve 30 moves toward the locking position over the leg retention sleeve 14, it forces the spring arms 32 and 34 together and the arcuate latch members engage the locking projections. As the locking sleeve reaches the full locking position of FIG. 1, the arcuate latch members slide into slots 40 in the locking sleeve and the leg retention sleeve is positively locked to the anchor support hub. However, as the locking sleeve is moved longitudinally away from the leg retention sleeve, the arcuate configuration of the latch members 36 permits them to slip out of the slots 40, and as the locking sleeve moves further, the spring arms 32 move outwardly causing the arcuate latch members to disengage the locking projections 38.

The locking sleeve 30 is mounted for movement toward and away from a centering shaft 42 which extends from a distal end 44 adjacent to the vena cava filter 10 back to the entry end of the catheter 22. The distal end of the centering shaft is formed with a plurality of spaced lumens 46, each of which mounts one of a plurality of centering arms 48. The centering shaft moves these centering arms out of the catheter 22 behind the vena cava filter, and these centering arms then expand outwardly to engage the vessel wall and center the leading end of the filter. These centering arms can be formed of spring metal or plastic, but are preferably formed of shape memory material such as nitinol.

To control the positioning of the vena cava filter 10 and subsequent ejection of the anchors 28 from the second open ends of the legs 12, an elongate drive shaft 50 extends from the entry or proximal end 52 of the catheter 22 through the catheter to a releasable connection 54 with the anchor support hub 20. This releasable connection can be any suitable connection which facilitates release of the drive shaft from the anchor support hub by manipulation of the drive shaft at the proximal end of the catheter such as a threaded connector as shown, a hook and eye connector, engaging hook connectors, and known twist engagement and release connectors. This drive shaft passes through the centering shaft 42 and is both rotationally and longitudinally movable relative thereto.

Figure 4:
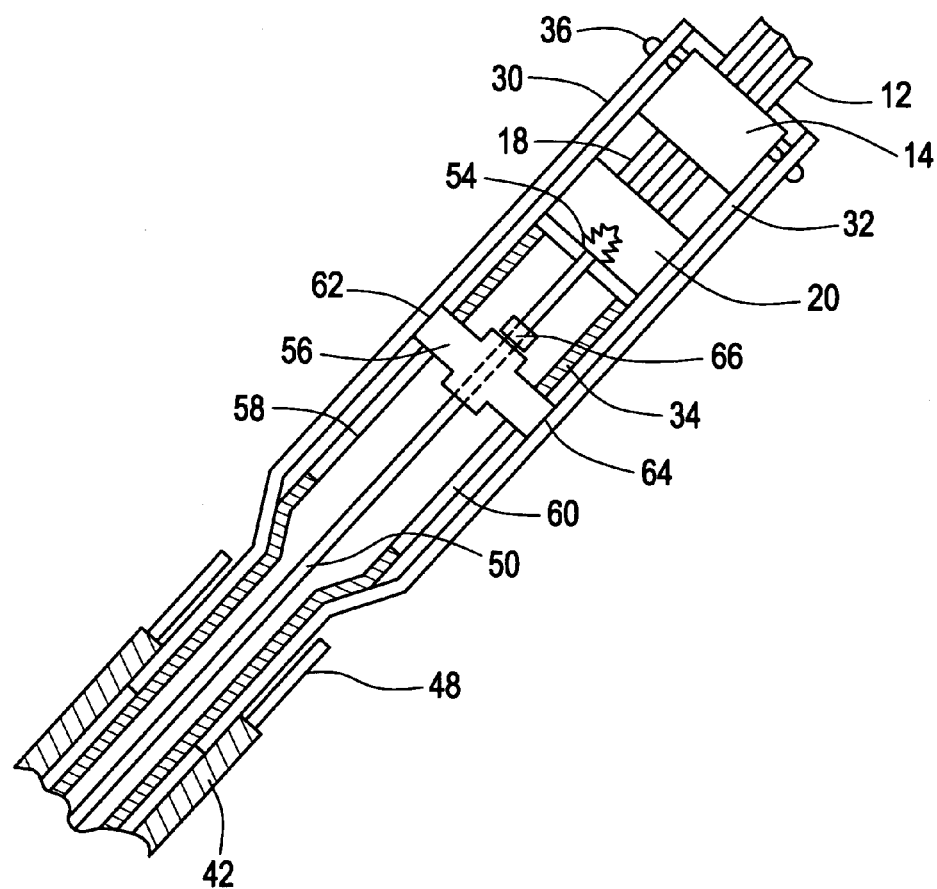
FIG. 4 is a sectional view showing the operating mechanism for the locking sleeve and anchor support hub of FIG. 1.

As shown in FIG. 4, the drive shaft passes through and is both rotationally and longitudinally movable relative to a locking sleeve operator 56 which passes through slots 58 and 60 in the housing 34. The locking sleeve operator is secured at 62 and 64 to the locking sleeve 30 and operates to move the locking sleeve away from the leg retention sleeve 14 as the locking sleeve operator moves away from the leg retention sleeve in the slots 58 and 60. The drive shaft operates to move the locking sleeve from the locked position by means of a stop 66 secured to the drive shaft and positioned to engage the locking sleeve operator.

When the catheter 22 reaches a desired position within a blood vessel, the vena cava filter 10 and centering arms 48 are exposed by either ejecting them from the catheter or drawing the catheter back from around them. Now the elongate legs 12 and centering arms 48 will expand outwardly into engagement with the vessel wall. However, the anchors 28 will remain enclosed within the elongate legs, and this permits the vena cava filter to be moved relative to the blood vessel after expansion of the elongate legs until an exact position is attained. If a substantial position change is required, the centering arms and vena cava filter can be drawn back into the catheter and subsequently redeployed in a new position.

Figure 5:
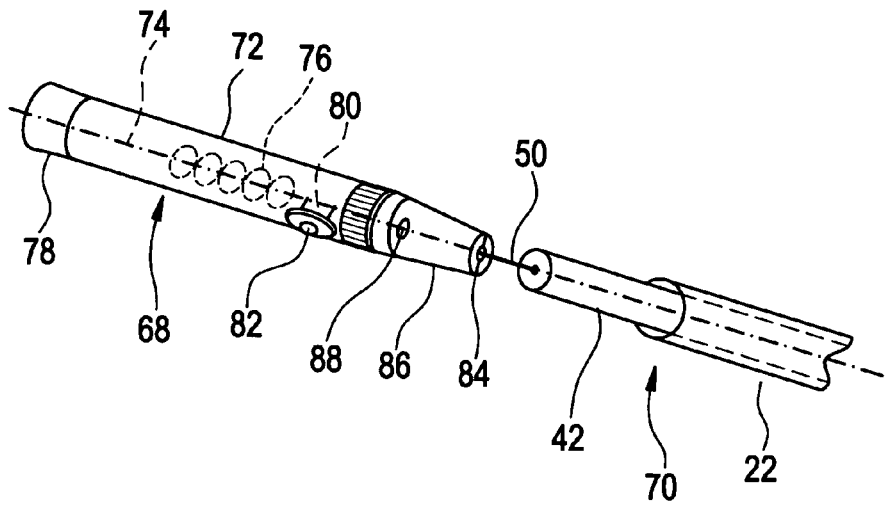
FIG. 5 is a perspective view showing a spring powered triggering unit at the proximal end of the catheter of FIG. 1 for propelling the anchor support hub.

With the vena cava filter in the desired position within a blood vessel and the elongate legs 12 engaging the vessel wall, the anchors 28 are now positively ejected out from the second open ends 26 of the elongate legs so as to penetrate through the vessel wall. To achieve this positive ejection of the anchors subsequent to engagement of the elongate legs with the vessel wall with sufficient force to result in penetration of the vessel wall, the drive shaft 50 is connected to a triggering unit 68 at the proximal or entry end 70 of the catheter 22. This triggering unit can be formed by a number of known units capable of imparting a longitudinal force to the drive shaft. An electrically powered solenoid unit can be used for this purpose as well as a number of spring powered units. In FIG. 5, the triggering unit is formed by a conventional ballistic-type lancer of the type commonly used to cause a needle to puncture a patient's skin to provide a blood sample. Such lancers include a hollow body 72 which contains a plunger 74 capable of moving axially back and forth within the body. The plunger is surrounded by a coil spring 76 which becomes compressed when the plunger is pulled back and armed by an end knob 78. The armed plunger is held in place by a trigger 80 which is activated to release the plunger by a button 82. When the plunger is released, the coil spring 76 propels the plunger toward an opening 84 in a nose cap 86 attached to the hollow body. For normal use of the ballistic type lancer, a needle is secured to the end 88 of the plunger and is propelled by the released plunger out through the opening 84 and into the skin of a patient. In FIG. 5, the drive shaft 50 is secured to the end 88 of the plunger, and when the armed plunger is released, the drive shaft is propelled longitudinally to drive the anchor support hub 20 toward the leg retention sleeve 14. This causes the long shafts 18 to move longitudinally through the elongate legs 12 to propel the anchors out and through the vessel wall. FIG. 6 illustrates an expanded vena cava filter 10 with the anchors 28 in the configuration that they would assume after passing through the vessel wall. The structure and operation of these anchors will be subsequently described.

A significant advantage of the vena cava filter 10 is that it can be repositioned even after the anchors are in place without the necessity to withdraw the complete filter back into the catheter 22. So long as the elongate legs are in contact with the vessel wall, the anchors 28 can be withdrawn from the vessel wall and back into the elongate legs by causing the drive shaft 50 to move the anchor support hub 20 away from the leg retention sleeve 14. Now the vena cava filter can be repositioned, the plunger 74 of the triggering unit 68 can be rearmed, and the anchors can again be ejected to pierce the vessel wall.

Once the vena cava filter 10 is properly positioned and anchored within a blood vessel, the drive shaft 50 is disconnected from the anchor support hub 20 and is pulled away from the anchor support hub causing the stop 66 to engage and move the locking sleeve operator 56 away from the anchor support hub. This results in movement of the locking sleeve 30 away from the leg retention sleeve 14 so that the spring arms 32 spring outwardly and the latch members 36 disengage from the locking projections 38. Now the centering shaft 42, locking sleeve 30, drive shaft 50 and housing 34 may be drawn back through the catheter 22 leaving the vena cava filter in place within the blood vessel.

To subsequently remove a previously anchored vena cava filter, the drive shaft 50 or a similar shaft is connected to the releasable connection 54 and is used to move the anchor support hub 20 longitudinally away from the leg retention sleeve 14. This draws the anchors 28 out of the blood vessel wall. Continued withdrawal force from the shaft will now cause the entire vena cava filter to be drawn into a catheter or delivery tube for removal.

The anchors 28 are formed at the proximal ends of the long shafts 18, and within the elongate legs 12 the anchors assume the same configuration as the shafts with which they are integrally formed. The shafts conform in configuration to the internal configuration of the elongate legs so as to easily move longitudinally within the elongate legs, and usually the shafts will be cylindrical with a pointed end which forms the leading end of the anchor. An enlarged view of the anchor of FIG. 6 is shown in FIG. 7.

Figure 7:
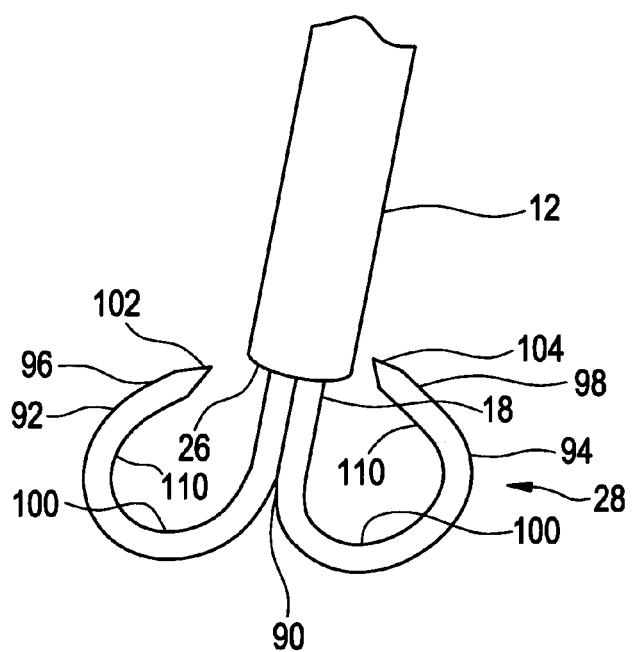
FIG. 7 is a perspective view of a deployed anchor for the blood clot filter of FIG. 6.

Referring to FIG. 7, the tubular shaft 18 is split down the center at 90 to form the opposed arms 92 and 94 of the anchor. The inner surfaces 96 and 98 of each of the arms is flat while the remaining surface 100 of each arm is arcuate, so that when the inner surfaces of the arms are contacting, a straight tubular end section is formed on the end of each long shaft 18. The pointed end of each long shaft forms the pointed ends 102 and 104 on the arms 92 and 94 of the anchor.

The expanded shape memory configuration of the anchors 28 is shown in FIGS. 6 and 7. Each anchor with the inner surfaces 96 and 98 in contact is ejected from an elongate leg 12 in a straight configuration when the anchor support hub 20 is driven toward the leg retention sleeve 14. The pointed lead end of each anchor will pierce the wall of a blood vessel so that the entire anchor passes through the vessel wall, at which point the anchor expands to its shape memory configuration shown in FIG. 7. Now the end 26 of the elongate leg engages the inner surface of the blood vessel wall while the pointed ends 102 and 104 of the arms 92 and 94 engage the outer surface of the blood vessel wall. It is important to note that portions of the expanded anchor, in this case the arms 92 and 94, extend outwardly on opposite sides of the shaft 18 so that forces in either direction in the plane of the anchor arms will not dislodge the anchor in the manner which can occur with a single hook which extends outwardly in only one direction from a support shaft. To provide additional protection from accidental dislodgement, the anchors 28 are oriented as shown in FIG. 7 so that the opposed arms 92 and 94 of the anchor expand transversely to the longitudinal direction 106 of blood flow through the filter 10. Thus the forces created by direct or reverse blood flow cannot dislodge the anchor, but since the anchor arms are each formed from half of a shaft 18 of a very small diameter, a withdrawal force along the longitudinal axis of the shaft will permit the anchor arms to come together to facilitate anchor withdrawal from the vessel wall.

It is important to note that the anchor arms 92 and 94 curve outwardly and back toward the shaft 18 to engage the outside surface of the vessel wall. This causes the anchor to be loaded in compression against the vessel wall when forces normal to the longitudinal axis of the vessel are applied to a medical device attached to the anchor. This compression aspect greatly enhances the anchoring function provided by the anchor and facilitates the effective use of very small, fine anchor components.

Figure 8:
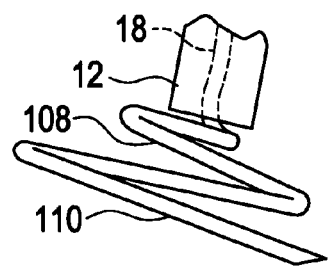
FIG. 8 is a perspective view of a second embodiment of a deployed anchor of the present invention.

The anchors 28 may take a number of forms so long as the anchor expands from a straight configuration from within an elongate leg 12 to a shape memory configuration where the anchor extends outwardly on at least two opposite sides of the shaft 18. In FIG. 8, the anchor 28 expands to a spiral cofiguration so as to extend completely around the shaft 18. Here the shaft is not split as shown in FIG. 7, but instead the intact end of the shaft is used to form the spiral 108. In all cases, first end of the anchor to emerge from an elongate leg 12 is a straight section 110 bearing the anchor point, and this section passes through a blood vessel wall before following sections which will form curves emerge. Both the anchors of FIGS. 7 and 8 tend to flatten by spring action against the vessel wall after expanding.

To form the anchor 28 of FIG. 9, the shaft 18 is flattened at the end and split at 90 to form two opposed, flat arms 112 and 114 which expand outwardly on opposite sides of the shaft. These arms emerge from the elongate leg 12 as a straight section which passes through the vessel wall and then splits and bends outwardly at 116 and 118 to form the arms. These arms lie against the outer surface of the vessel walland in a vena cava filter, are oriented transverse to the longitudinal direction of blood flow through the filter.

For some medical applications, a need has arisen for a single anchor to tether a device within a body vessel or to a body wall. An apparatus similar to that previously described with reference to the multiple anchor vena cava filter 10 can be employed to deploy the single anchor 120 of FIG. 10. The single anchor 120 is formed at the distal end of an anchor shaft 122 mounted in an elongate tube 124, Both the shaft 122 and the tube 124 are formed of shape memory material as described relative to the elongate legs 12 and long shafts 18, but are normally much shorter in length than the elongate legs and shafts 18. A tube retention sleeve 126 retains the single tube 124 in the same manner that the leg retention sleeve 14 operates to retain the elongate legs 12, and this tube retention sleeve is engaged by a locking sleeve (not shown) and spring arms 32 operative in the manner previously described. A drive shaft 50 is connected at the entry end of the catheter 22 to a triggering unit 68, and is also connected to a releasable connection 128 similar to the releasable connection 54. This releasable connection is firmed in a shaft support hub 130 normally spaced from the tube retention sleeve 126 which is connected to the proximal end of the anchor shaft.

The drive shaft 50 is movable in a control shaft 132 similar to the centering shaft 42 which operates to move the shaft support hub and tube retention sleeve longitudinally to expel the tube 124 containing the anchor 120 from the catheter 22. The tube 124 will now assume a predetermined shape to position the anchor relative to a body wall which will receive the anchor. Now the triggering unit 68 can be operated to cause the drive shaft 50 to move the shaft support hub 130 toward the tube retention sleeve 126 to drive the anchor 120 through the body wall. The anchor 120 is formed of shape memory material and can take the form and operate in the manner of any of the anchors previously described. Once the anchor is delivered, the spring arms 32 can be operated to release the tube retention sleeve 126, and the drive shaft can be released from the releasable connection 128 so that the drive and control shafts, and in some cases the catheter, can be withdrawn. If the purpose of the anchor is to anchor the catheter in position, then a tether 134 is provided between the catheter and the anchor, and the catheter will not be withdrawn with the drive and control shafts.

In some instances, the catheter 22 may be a dual lumen catheter having a first lumen 136 containing the described anchor mechanism and a second lumen 138 containing an implant able medical device 140 to be anchored by the anchor 120. In this case, a tether 142 is connected between the anchor and the implant able medical device, and once the anchor is in place, the implant able medical device is ejected from the catheter.

When it is possible to use the catheter to properly position the anchor 120 relative to a body wall, the tube 124 and tube retention sleeve 126 can be eliminated and replaced by the catheter lumen. Now the drive shaft 50 will drive the shaft support hub 130 longitudinally to drive the anchor from the catheter lumen and through the body wall.

We claim:

1. A medical device anchor for penetration through a body wall from a first side to a second side thereof and expansion against said second side comprising:

an anchor shaft having a proximal end, a distal end and a longitudinal axis, an expandable anchor at the distal end of said anchor shaft having anchor sections formed integrally with said anchor shaft by splitting said anchor shaft longitudinally at the distal end thereof to form first and second anchor sections, said expandable anchor having a first collapsed configuration wherein said anchor is substantially coextensive with said anchor shaft and a second expanded configuration wherein said first and second anchor sections extend outwardly from said anchor shaft in opposite directions transverse to the longitudinal axis of said anchor shaft, said first and second anchor sections curve arcuately outward from said anchor shaft and back toward said anchor shaft in the second expanded configuration of said expandable anchor.

2. The medical device anchor of claim 1 wherein said expandable anchor includes a pointed lead end.

3. The medical device anchor of claim 1 wherein said expandable anchor is formed of shape memory material which is compliable and compressible in a first state and which is self-expandable in a second state to a substantially rigid, predetermined spiral configuration.

4. A medical device anchor and delivery system for propelling an anchor through a body wall form a first side to a second side where said anchor expands against said second side comprising:

an anchor shaft having a proximal end, a distal end and a longitudinal axis, an expandable anchor at the distal end of said anchor shaft having anchor sections formed integrally with said anchor shaft by splitting said anchor shaft longitudinally at the distal end thereof to form first and second anchor sections, said expandable anchor having a first collapsed configuration where said anchor is substantially coextensive with said anchor shaft and a second expanded configuration wherein said first and second anchor sections extend outwardly from said anchor shaft in at least two opposed directions transverse to the longitudinal axis of said anchor shaft, said first and second anchor sections curve arcuately outward from said anchor shaft and back toward said anchor shaft in the second expanded configuration of said expandable anchor, a shaft support hub connected to the proximal end of said anchor shaft an elongate tube having an entry and an exit end, said tube containing said anchor shaft with said expandable anchor in said collapsed configuration adjacent to said exit end, and a drive shaft having a first end in engagement with said shaft support hub and operative when propelled to cause said shaft support hub to move said anchor shaft longitudinally of said elongate tube to propel said expandable anchor outwardly from the exit end of said tube, said drive shaft including a second end opposite to said first end, the second end being connection to a propulsion unit operative to propel said drive shaft.

5. The medical device anchor and delivery system of claim 4 wherein said anchor shaft has a longitudinal axis and wherein said first and second anchor sections expand outwardly from said anchor shaft in opposite directions and transverse to the longitudinal axis of said anchor shaft in the second expanded configuration of said expandable anchor.

6. The medical device anchor and delivery system of claim 5 wherein said expandable anchor is formed of thermal shape memory material having temperature transformation level where at temperatures below said temperature transformation level said shape memory material is relatively pliable and compressible and at temperatures at least at or above said temperature transformation level said shape memory material is self-expandable to a substantially rigid predetermined configuration.

7. A blood clot filter with an anchor delivery system for propelling one or more anchors through the wall of a blood vessel from a first inner side to a second outer side, the blood clot filter having a central longitudinal axis and being collapsible to a collapsed configuration toward said longitudinal axis and expandable to an expanded configuration outwardly from said longitudinal axis for contact with the inner side of the wall of said blood vessel, said blood clot filter comprising:

a plurality of elongate, spaced legs each having a distal end and a proximal end, the proximal ends of said elongate legs being secured together adjacent to the longitudinal axis of said blood clot filter, said plurality of elongate spaced legs being formed to extend outwardly away from said longitudinal axis to bring the distal ends thereof into contact with the first inner side of a blood vessel in the expanded configuration of said blood clot filter, one or more of said elongate spaced legs being tubular in configuration with an open distal and an open proximal end, an elongate anchor shaft positioned for longitudinal movement in each of said tubular elongate legs, each said elongate anchor shaft having first and second opposed ends, an expandable anchor at the second end of each of said anchor shafts, said expandable anchor having one or more anchor sections with a first collapsed configuration wherein said anchor is substantially coextensive with said anchor shaft and a second expanded configuration wherein said one or more anchor sections extend outwardly from said anchor shaft in at least two opposed directions, said tubular elongate legs each containing said expandable anchor in the first collapsed condition adjacent to the open distal end thereof, a shaft support hub connected to the first end of each elongate anchor shaft, said shaft support hub being spaced from the proximal ends of said elongate legs when an expandable anchor in the first collapsed condition is contained in said tubular elongate legs, said shaft support being moveable toward the proximal ends of said elongate legs to move said anchor shafts longitudinally to propel said expandable anchors out from the open distal ends of said tubular elongate legs and through the wall of a blood vessel, and each said expandable anchor includes first and second anchor sections which expand outwardly from said anchor shaft in opposite directions when said expandable anchor is propelled out from the open distal end of a tubular elongate leg and through the wall of a blood vessel, said expandable anchor being oriented such that the first and second anchor sections expand in directions transverse to the longitudinal axis of said blood clot filter.

8. The blood clot filter with anchor delivery system of claim 7 which includes a drive shaft having a first drive shaft end connected to said shaft support hub to move said shaft support hub relative to the proximal ends of said elongate legs.

9. The blood clot filter with anchor delivery system of claim 8 wherein said drive shaft is positioned for movement within an elongate filter centering shaft having an inner end spaced adjacent to said shaft support hub, said filter centering shaft having a plurality of elongate, spaced, centering arms secured at one end to said centering shaft inner end, said centering arms being adapted to expand outwardly into engagement with said blood vessel wall inner side.

10. The blood clot filter with anchor delivery system of claim 9 wherein said drive shaft includes a second drive shaft end opposite to said first drive shaft end, said second drive shaft end being connected to a propulsion device to cause said drive shaft to propel said shaft support hub toward the proximal ends of said elongate legs.

11. The blood clot filter with anchor delivery system of claim 7 wherein said expandable anchor, anchor shaft and plurality of elongate spaced legs are formed of thermal shape memory material.

12. A blood clot filter with an anchor delivery system for propelling one or more anchors through the wall of a blood vessel from a first inner side to a second outer side, the blood clot filter having a central longitudinal axis and being collapsible to a collapsed configuration toward said longitudinal axis and expandable to an expanded configuration outwardly from said longitudinal axis for contact with the inner side of the wall of said blood vessel, said blood clot filter comprising:
  a plurality of elongate, spaced legs each having a distal end and a proximal end the proximal ends of said elongate legs being secured together adjacent to the longitudinal axis of said blood clot filter, said plurality of elongate spaced legs being formed to extend outwardly away from said longitudinal axis to bring the distal ends thereof into contact with the first inner side of a blood vessel in the expanded configuration of said blood clot filter, one or more of said elongate spaced legs being tubular in configuration with an open distal and an open proximal end,
  an elongate anchor shaft positioned for longitudinal movement in each of said tubular elongate legs, each elongate anchor shaft having first and second opposed ends, an expandable anchor at the second end of each of said anchor shafts, said expandable anchor having one or more anchor sections with a first collapsed configuration wherein said anchor is substantially coextensive with said anchor shaft and a second expanded configuration wherein said one or more anchor sections extend outwardly from said anchor shaft in at least two opposed directions, said expandable anchor is configured to extend outwardly from said anchor shaft in a spiral configuration in the second expanded configuration of said anchor;
  said tubular elongate legs each containing said expandable anchor in the first collapsed condition adjacent to the open distal end thereof, and a shaft support hub connected to the first end of each elongate anchor shaft, said shaft support hub being spaced from the proximal ends of said elongate legs when an expandable anchor in the first collapsed condition is contained in said tubular elongate legs, said shaft support being moveable toward the proximal ends of said elongate legs to move said anchor shafts longitudinally to propel said expandable anchors out from the open distal ends of said tubular elongate legs and through the wall of a blood vessel.

13. A blood clot filter with an anchor delivery system for propelling one or more anchors through the wall of a blood vessel from a first inner side to a second outer side, the blood clot filter having a central longitudinal axis and being collapsible to a collapsed configuration toward said longitudinal axis and expandable to an expanded configuration outwardly from said longitudinal axis for contact with the inner side of the wall of said blood vessel, said blood clot filter comprising:
  a plurality of elongate, spaced legs each having a distal end and a proximal end, the proximal ends of said elongate legs being secured together adjacent to the longitudinal axis of said blood clot filter, said plurality of elongate spaced legs being formed to extend outwardly away from said longitudinal axis to bring the distal ends thereof into contact with the first inner side of a blood vessel in the expanded configuration of said blood clot filter, one or more of said elongate spaced legs being tubular in configuration with an open distal end and an open proximal end,
  an elongate anchor shaft positioned for longitudinal movement in each of said tubular elongate legs, each elongate anchor shaft having first and second opposed ends, an expandable anchor at the second end of each of said anchor shafts, said expandable anchor having one or more anchor sections with a first collapsed configuration wherein said anchor is substantially coextensive with said anchor shaft and a second expanded configuration wherein said one or more anchor sections extend outwardly from said anchor shaft in at least two opposed directions, the expandable anchor at the second end of each anchor shaft is formed integrally with the anchor shaft by splitting the anchor shaft longitudinally in the second end thereof to form first and second anchor sections,
  said tubular elongate legs each containing said expandable anchor in the first collapsed condition adjacent to the open distal end thereof, and
  a shaft support hub connected to the first end of each elongate anchor shaft, said shaft support hub being spaced from the proximal ends of said elongate legs when an expandable anchor in the first collapsed condition is contained in said tubular elongate legs, said shaft support being moveable toward the proximal ends of said elongate legs to move said anchor shafts longitudinally to propel said expandable anchors out from the open distal ends of said tubular elongate legs and through the wall of a blood vessel.

14. The blood clot filter with anchor delivery system of claim 13 wherein said anchor shaft has a longitudinal axis, and wherein said first and second anchor sections expand outwardly from said anchor shaft in opposite directions and transverse to the longitudinal axis of said anchor shaft in the second expanded configuration of said expandable anchor.

15. The blood clot filter with anchor delivery system of claim 14 wherein each said expandable anchor is oriented such that said first and second anchor sections expand in directions transverse to the longitudinal axis of said blood clot filter.

16. The blood clot filter with anchor delivery system of claim 14 wherein said first and second anchor sections when expanded curve arcuately outward from said anchor shaft and back toward the anchor shaft.

17. A blood clot filter with an anchor delivery system for propelling one or more anchors through the wall of a blood vessel from a first inner side to a second outer side, the blood clot filter having a central longitudinal axis and being collapsible to a collapsed configuration toward said longitudinal axis and expandable in an expanded configuration outwardly from said longitudinal axis for contact with the inner side of the wall said blood vessel, said blood clot filter with anchor delivery system comprising:

a plurality of elongate legs each having a proximal end and a distal end section terminating at a distal end, the proximal ends of said elongate legs being secured together adjacent to the longitudinal axis of said blood clot filter, said elongate legs being formed to extend outwardly away from said longitudinal axis to bring at least a portion of the distal end sections thereof into contact with a first inner side of the wall of a blood vessel in the expanded configuration of said blood clot filter, one or more of said elongate legs having an open proximal end, an exit opening formed in said leg in the distal end section thereof, and an internal passageway extending between said open proximal end and said exit opening, one or more anchor shafts having first and second opposed ends, an expandable anchor at the second end of each said anchor shaft having one or more anchor sections, said expandable anchor having a first configuration wherein said anchor is substantially coextensive with said anchor shaft and a second expanded configuration wherein said one or more anchor sections extend outwardly from said anchor shaft, an anchor shaft being positioned for longitudinal movement in the internal passageway of said one or more elongate legs with the expandable anchor in the collapsed configuration adjacent to said exit opening, the first end of each said anchor shaft extending outwardly from the proximal ends of said elongate legs when the expandable anchor is in the collapsed configuration adjacent to the exit opening, and a drive unit including a locking unit in engagement with said proximal ends of said elongate legs to lock said elongate legs against longitudinal movement relative to said one or more anchor shafts, and a drive shaft positioned, for longitudinal movement toward the proximal ends of said elongate legs to engage the first end of said one or more anchor shafts to move each anchor shaft longitudinally toward the distal end of said one or more elongate legs to propel each expandable anchor out through an exit opening and through the blood vessel wall.

18. The blood clot filter and anchor delivery system of claim 17 wherein said one or more elongate legs are connected to a retention sleeve at the proximal ends thereof, said locking unit engaging said retention sleeve to lock said one or more elongate legs against longitudinal movement relative to said one or more anchor shafts.

19. The blood clot filter and anchor delivery system of claim 18 wherein said locking unit includes a releasable lock for engaging said retention sleeve.

20. The blood clot filter and delivery system of claim 18 wherein the first ends of said one or more anchor shafts extend outwardly from the open proximal end of said one or more elongate legs to a shaft support hub spaced from said retention sleeve when the expandable anchor connected to each anchor shaft is in said collapsed configuration in said internal passageway.

21. The blood clot filter and anchor delivery system of claim 20 wherein said drive shaft has a first drive shaft end in engagement with said shaft support hub, said drive shaft being positioned for longitudinal movement to cause said shaft support hub to move toward said retention sleeve to cause said one or more anchor shafts to move toward the distal ends of said one or more elongate legs to propel each said expandable anchor out through an exit opening and through the wall of a blood vessel.

22. The blood clot filter and anchor delivery system of claim 21 wherein said drive shaft includes a second drive shaft end spaced from said first drive shaft end, said second drive shaft end being connected to a propulsion unit operative to propel said drive shaft longitudinally to drive said shaft support hub toward said retention sleeve.

23. The blood clot filter and anchor delivery system of claim 21 wherein said locking unit includes an elongate filter centering shaft having a releasable lock at an inner end thereof for engagement with said retention sleeve, said releasable lock for said elongate filter centering shaft engaging said retention sleeve to permit said filter centering shaft to move said blood clot filter into a blood vessel and to prevent longitudinal movement of said one or more elongate legs during longitudinal movement of said one or more anchor shafts toward the distal ends of said elongate legs, said drive shaft being positioned for longitudinal movement within said filter centering shaft.

24. The blood clot filter and anchor delivery system of claim 17 wherein said one or more anchor sections curve arcuately outward from each said anchor shaft and back toward said anchor shaft in the second expanded configuration of said expandable anchor.

25. The blood clot filter and anchor delivery system of claim 17 wherein said locking unit includes an elongate filter centering shaft having a releasable lock at an inner end thereof to engage said elongate legs to permit said filter centering shaft to move said blood clot filter into a blood vessel and to prevent longitudinal movement of said one or more elongate legs during longitudinal movement of said one or more anchor shafts toward the distal ends of said elongate legs, said drive shaft being positioned for longitudinal movement within said filter centering shaft.

26. A method for positioning and anchoring a blood clot filter having a plurality of elongate spaced legs adapted to expand outwardly from a filter longitudinal axis to bring at least a portion of a free end section of each of said legs into contact with the inner surface of a blood vessel wall having an inner and outer surface, the free end section of each of said legs terminating at a free end for said leg, the method including:

enclosing an elongate anchor shaft and an expandable anchor in a non expanded state for longitudinal movement within one or more of said elongate spaced legs, each said expandable anchor being connected to a distal end section of an anchor shaft and positioned in the non expanded state in the free end section of an elongate leg, causing the elongated spaced legs to collapse toward the longitudinal axis of said blood clot filter, transporting said blood clot filter with the elongate spaced legs collapsed and with one or more of said elongate legs enclosing an expandable anchor in the non expanded state through a blood vessel to a desired position, at the desired position, causing said elongate spaced legs to expand to bring at least a portion of the free end sections thereof into contact with the inner surface of the blood vessel wall, subsequent to contact of said free end sections with the inner surface of the blood vessel wall, propelling each said expandable anchor in the non expanded state and the distal end section of the anchor shaft to which the anchor is connected out of the free end section of an elongate leg through an exit opening formed in the free end section and through the inner and outer surfaces of the blood vessel wall, and causing each said anchor to expand laterally from the distal end section of the anchor shaft to which the anchor is connected against the outer side of the blood vessel wall.

27. The method of claim 26 which includes restraining said elongate spaced legs against movement in the direction of the free ends thereof while propelling said expandable anchors out of the free end section thereof.

28. The method of claim 27 which includes causing said expandable anchor to expand in two opposite directions which are transverse to the longitudinal axis of said blood clot filter and engage against the outer surface of the blood vessel wall.

29. The method of claim 26 which includes causing each said anchor to expand laterally from the distal end section of an anchor shaft and to engage the outer surface of the blood vessel wall in at least two spaced locations without puncturing the outer surface of the blood vessel wall.

30. The method of claim 29 which includes causing each said expandable anchor to expand laterally outward from the distal end section of an anchor shaft in an arcuate configuration and to curve back toward said anchor shaft to engage against the outer side of the blood vessel wall at two or more spaced locations.

31. The method of claim 27 which includes causing each said anchor to expand laterally from the distal end section of the anchor shaft to which the anchor is connected and to engage to outer surface of the blood vessel wall in at least two spaced locations.

32. The method of claim 31 which includes causing each expandable anchor to expand laterally from the distal end section of the anchor shaft to which the anchor is connected in an arcuate configuration and to curve back toward said anchor shaft to engage against the outer side of the blood vessel wall at two or more spaced locations.

33. A blood clot filter with an anchor delivery system for propelling one or more anchors through the wall of a blood vessel from a first inner side to a second outer side, the blood clot filter having a longitudinal axis and being collapsible to a collapsed configuration toward said longitudinal axis and expandable in an expanded configuration outwardly from said longitudinal axis for contact with the inner side of the wall of said blood vessel, said blood clot filter with anchor delivery system comprising:

a plurality of elongate legs each having a proximal end and a distal end section terminating at a distal end, the proximal ends of said elongate legs being secured together adjacent to the longitudinal axis of said blood clot filter, said elongate legs being formed to extend outwardly away from said longitudinal axis to bring at least a portion of the distal end sections thereof into contact with a first inner side of the wall of a blood vessel in the expanded configuration of said blood clot filter, one or more of said elongate legs having an open proximal end, an exit opening formed in said leg in the distal end section thereof, and an internal passageway extending between said open proximal end and said exit opening, one or more anchor shafts having first and second opposed ends with a second end section terminating at said second end, an expandable anchor at the second end of each said anchor shaft having one or more anchor sections, said expandable anchor having a first collapsed configuration wherein said anchor is substantially coextensive with said anchor shaft and a second expanded configuration wherein said one or more anchor sections extend outwardly from said anchor shaft, an anchor shaft being positioned for longitudinal movement in the internal passageway of said one or more elongate legs with the expandable anchor in the collapsed configuration adjacent to said exit opening, the first end of each said anchor shaft extending outwardly from the proximal ends of said elongate legs when the expandable anchor is in the collapsed configuration adjacent to the exit opening, and a drive unit including a drive shaft positioned for longitudinal movement toward the proximal ends of said elongate legs to engage the first end of said one or more anchor shafts to move each anchor shaft longitudinally toward the distal end of said one or more elongate legs to propel each expandable anchor out through an exit opening and through the blood vessel wall, the first end of each anchor shaft extending outwardly from the proximal end of an elongate leg when the anchor at the second end thereof is in the collapsed configuration within an elongate leg for a distance sufficient to cause said expandable anchor and the second end section of said anchor shaft to be propelled out through an exit opening and through the wall of a blood vessel from the first inner side to the second outer side.

34. The blood clot filter and anchor delivery system of claim 33 wherein said drive unit includes a locking unit in engagement with the proximal ends of said elongate legs to lock said elongate legs against longitudinal movement relative to said one or more anchor shafts during longitudinal movement of said anchor shafts.

35. The blood clot filter and anchor delivery system of claim 33 wherein each said anchor is formed to curve outwardly from the second end of said anchor shaft and back toward the second end section of said anchor shaft in the second expanded configuration of said anchor.

36. The blood clot filter and anchor delivery system of claim 33 wherein each said anchor is formed to engage the second outer side of a blood vessel wall in at least two spaced locations in the second expanded configuration of said anchor.

* * * * *